Figure 1:
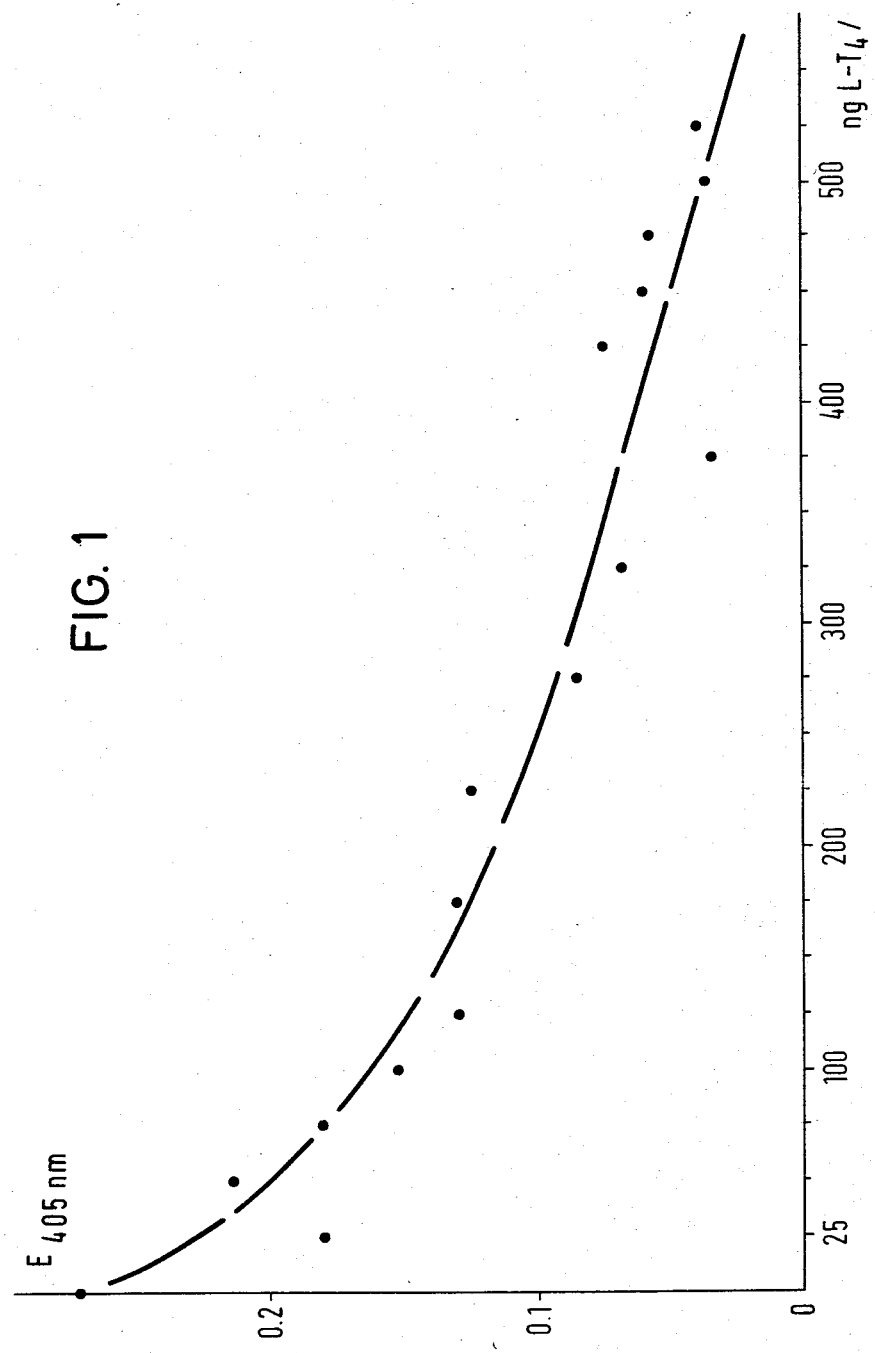

United States Patent [19]

Schrenk

[11] Patent Number: 4,510,240

[45] Date of Patent: Apr. 9, 1985

[54] HOMOGENEOUS ENZYME IMMUNOASSAY WITH HEATING STEP AFTER INCUBATION, THERESIA

[75] Inventor: Jürgen Schrenk, Wilzhofen, Fed. Rep. of Germany

[73] Assignee: Boehringer Mannheim GmbH, Mannhein-Waldhof, Fed. Rep. of Germany

[21] Appl. No.: 409,278

[22] Filed: Aug. 18, 1982

[30] Foreign Application Priority Data

Aug. 31, 1981 [DE] Fed. Rep. of Germany ....... 3134361

[51] Int. Cl.$^3$ ............................................. G01N 33/54
[52] U.S. Cl. ....................................... 435/7; 436/536; 436/537
[58] Field of Search ..................... 435/7; 436/536, 537

[56] References Cited

U.S. PATENT DOCUMENTS 4,341,866  7/1982  Yoshida ................................. 435/7

OTHER PUBLICATIONS

"Enzyme–Immunoassay", E. T. Maggio, ed., Chapt. 5, pp. 105–134, by E. F. Ullman et al., CRC Press, Boca Raton, (1980).

Primary Examiner—Sidney Marantz
Attorney, Agent, or Firm—Felfe & Lynch

[57] ABSTRACT

A process for the determination of an antigen or hapten in homogeneous aqueous phase by incubation in the presence of antigen- or hapten-specific antibodies and of a definite amount of enzyme-marked antigen or hapten and measurement of the activity of the marker enzyme, wherein, after incubation, the reaction solution is heated under those temperature conditions and for a period of time at which the marker enzyme is inactivated by at least 50% in the absence of the antigen- or hapten-specific antibody and the enzyme activity thereafter measured.

Also a reagent for carrying out this process, wherein it contains a definite amount of $\beta$-galactosidase-hapten conjugate, hapten antibody, buffer (pH 6.0 to 8.5), a system for the determination of the $\beta$-galactosidase activity and optionally a definite amount of $\beta$-galactosidase antibody.

6 Claims, 2 Drawing Figures

HOMOGENEOUS ENZYME IMMUNOASSAY WITH HEATING STEP AFTER INCUBATION, THERESIA

This invention relates to a method for the determination of antigens and haptens, using the enzyme-immuno technique in the homogeneous phase, and is also concerned with a reagent for carrying out this method.

Because of the continuously increasing number of clinical-chemical analyses of serum components and of similar biological materials, the automating of such methods is of increasing importance. Only by means of automating it is possible to deal with the considerably increasing number of such determinations and thereby also to reduce the necessary expenditure of labour per determination.

An important advance in clinical diagnosis was the development of processes for the determination of the components of immune reactions. Thus, by means of the method of radio-immune analysis (RIA), a substantial increase of the sensitivity of such determinations was achieved. A disadvantage of the RIA, namely, the necessity of having to deal with radioactive substances, was overcome by replacing the radioactive label by an enzyme marking, which resulted in the so-called enzyme-immuno assay (EIA). In the case of this process, a definite amount of an enzyme-marked component of an immune reaction is allowed to compete with the unmarked component to be determined and present in an unknown amount for the common component of the immune reaction, i.e. the specific binding protein or the substance bindable therewith. In the case of the so-called ELISA method, the binding component, for which the substance to be determined must compete with the enzyme-marked substance, is used in solid form in order to simplify the separation of free and bound enzyme-marked substance. However, when carrying out this heterogenous process in automatic analysers, problems arise which, as a rule, require additional devices.

It is also known to carry out the EIA in homogeneous phase in that the enzymatic activity of the antigen- or hapten-enzyme conjugate is influenced by the antigen-antibody reaction. It is assumed that the antibody hereby reduces the affinity of the enzyme substrate for the active part of the enzyme either by steric hindrance or by a conformation change of the enzyme or by preventing the conformation change necessary for the catalytic activity of the enzyme. A case is also known in which the marker enzyme is inhibited by the hapten coupled thereon but becomes reactive again by means of the appropriate antibody. However, these methods are only of limited use since hitherto only a few suitable enzyme-hapten combinations have been found in which a corresponding inhibition of the enzyme activity by one of the components of the immune reaction takes place.

Therefore, it is an object of the present invention to find a new method of analysis which offers not only the advantages of the high specificity of immune reactions but also the high detection sensitivity of marking enzymes, i.e. in general follows the EIA principle, can also be carried out in homogeneous phase but does not require the specific inhibition of the enzyme by the hapten or antigen or its antibody.

The influencing of the heat denaturability of marker enzymes bound to haptens or antigens by hapten- or antigen-specific antibodies serves to satisfy this object and to provide a solution of the problem according to the present invention.

Thus, according to the present invention, there is provided a process for the determination of an antigen or hapten in homogeneous aqueous phase by incubation in the presence of antigen- or hapten-specific antibodies and of a definite amount of enzyme-marked antigen or hapten and measurement of the activity of the marker enzyme, wherein, after incubation, the reaction solution is heated under those temperature conditions and for a period of time at which the marker enzyme is inactivated by at least 50% in the absence of the antigen- or hapten-specific antibody and the enzyme activity thereafter measured.

Consequently, we have called the process according to the present invention the THERESIA method (THErmoRESistance-Immuno-Assay).

The present invention is based upon the surprising discovery that antibodies which are not directed against the marker enzyme but against the hapten or antigen so influence the heat denaturability of the marker enzyme that a quantitative analytic determination can be based thereon.

In the case of the process according to the present invention, the conjugate of hapten or antigen and enzyme is added in a definite amount, i.e. in a known amount. In principle, the amount can admittedly be freely chosen but should be of the order of magnitude of the range of amounts coming into consideration for the hapten or antigen to be determined present in the sample solution since free hapten or antigen and the enzyme-marked derivative thereof must, of course, compete for the antibody.

The hapten-specific or antigen-specific antibody is also added in a definite amount, which depends upon the amount of added enzyme conjugate and can easily be ascertained by preliminary experiments. The amount is thereby such that it just suffices to prevent the heat denaturing of the marker enzyme.

The heat inactivation step itself is so chosen with regard to the temperature to be employed and the period of application thereof that the marker enzyme is inactivated by at least 50%. As is known, heat denaturing follows the general chemical laws and, in the case of increasing temperature, the period of the action necessary for the denaturing decreases accordingly. Thus, for example, in the case of $\beta$-galactosidase, a practically 100% inactivation can be achieved at 58° C. by the action of heat for 15 minutes and at 62° C. the action of heat for only 5 minutes is needed, in each case at a given pH and buffer value. The conditions of the heating step are thereby preferably so chosen that they just suffice in order to achieve the desired degree of inactivation. The simplest method of working is thereby obtained when a 100% inactivation is just to be achieved but the process can also be carried out to a degree of inactivation of down to 50%. The field of use is hereby considerably widened since even a slight influencing of the heat inactivation by the hapten- or antigen-specific antibody can be utilised for the process.

As marker enzymes, there can, in principle, be used the heat-denaturable and easily determinable enzymes. Markers enzymes are preferred which consist of at least two enzyme subunits, i.e. have several protein chains, examples of which include glucose oxidase, malate dehydrogenase, acetylcholine esterase, catalase and $\beta$-galactosidase, the latter being especially preferred.

As haptens, there can be used the physiological and non-physiological low molecular weight compounds which are of interest for the determination but which themselves are not capable of forming antibodies and the determination of which is clinically relevant. These include, for example, hormones, phamaceutically active materials, enzyme substrates and the like. Examples of non-physiological haptens include pharmaceuticals and similar substances. For antigens there applies, in principle, the same but they possess the ability themselves to bring about antibody formation, whereas in the case of the haptens, for this purpose, conjugates between hapten and immunogenic substance are necessary. All these definitions and processes are well known to the expert and do not require further explanation here. As examples of haptens or antigens which can be used within the scope of the present invention, there may be mentioned the thyroid hormones, natural and synthetic steroid hormones, digoxin and digitoxin, insulin, thyrotropin, ferritine, $\alpha_1$-foetoprotein, carcinoembryonic antigen, $HB_2$-antigen and the like.

The antibody formation takes place in known manner by immunising suitable experimental animals or by using cell cultures for obtaining the antiserum, which can either be used as such or after purification of the antibody. As a rule, the antiserum so obtained can be used directly but a purification of the antigen-specific or hapten-specific antibody can be carried out by the usual methods for this purpose, for example ammonium sulphate fractionation, immunosorption and the like, which can be used individually or together. In the case of the hapten, immunisation is carried out with a conjugate of the hapten with a substance suitable for the antibody formation. For this purpose, too, there can be used the substances known to the expert. Preferred are proteins, such as serum albumins of different origins, especially bovine serum albumin (BSA) and human serum albumin (HSA), as well as edestin. It is, of course, important that the immunogen is different from the marker enzyme used in order to be certain that no antibody against the marker enzyme is formed by the immunisation.

The measurement of the activity of the marker enzymes is carried out by methods known for this purpose and does not require detailed explanation.

As already mentioned, the above-described method depends upon the surprising stabilisation of the marker enzyme in the conjugate with the hapten or antigen against heat denaturing by the antibody not directed against the marker enzyme but against the hapten or antigen.

However, the process according to the present invention can also be used, with a slight change, when the hapten-specific or antigen-specific antibody is not able to bring about such a suppression of the heat inactivation. In this case, for the incubation there is additionally used an enzyme-specific antibody which is able to stabilise the enzyme against the normal heat denaturing. From Biochem. Biophys. Res. Comm., 40, 570–575/1970, it is admittedly already known that enzyme-specific antibodies are able to stabilise their enzymes against heat denaturing. However, it was not to have been foreseen that this stabilisation is again removed by hapten- or antigen-specific antibodies and, therefore, can also be used in the process according to the present invention. Thus, for example, we have found that digoxin antibody is not able to stabilise $\beta$-galactosidase itself against heat denaturing but that it prevents the stabilization of this enzyme by the $\beta$-galactosidase antibody.

In the case of that embodiment of the process according to the present invention which is carried out in the presence of the enzyme-specific antibody, the amount of enzyme-specific antibody and of hapten- or antigen-specific antibody is fixed as explained hereinafter. In this case, there is first determined that amount of enzyme-specific antibody which, under the given temperature and time conditions, prevents the heat inactivation of the enzyme and subsequently that amount of hapten- or antigen-specific antibody which again removes this stabilisation. In the presence of free hapten or antigen, which enters into a complex with its antibody, the heat stabilisation again becomes effective by the enzyme-specific antibody, namely, to the extent in which hapten- or antigen-antibody complexes have been formed.

The production of the enzyme-hapten or enzyme-antigen conjugate and of the hapten-immunogen conjugate is carried out by known methods, preferably with the use of bifunctional bridge building reagents, suitable methods being described, for example, in Annals of Chemical Biochemistry, 16, 221–239/1979.

The process according to the present invention has a very high sensitivity and, therefore, makes possible the determination of extremely small amounts of haptens and antigens, especially in the case of the embodiment in the presence of enzyme-specific antibodies. Thus, in the case of amounts of sample of the order of magnitude of only a few pg., it is possible to carry out the determination within a very short period of time: for the totality of the steps, i.e. incubation, heating step and enzyme determination, not more than 20 to 30 minutes are necessary. Since the process does not require any separation operations, it is outstandingly suitable for carrying out on commercially available automatic analysers. As a rule, the only change of apparatus which is necessary is the incorporation of a heating path if the automatic analyser does not already have one.

With regard to the pH value and the buffer substance used for the process according to the present invention, there apply the conditions required for the marker enzyme. This means that, depending upon the marker enzyme used, a pH value and a buffer substance are used which ensure a sufficient activity of the enzyme. These conditions are known for the enzymes coming into consideration.

The present invention also provides a reagent for carrying out the process according to the present invention, which contains a definite amount of $\beta$-galactosidase-hapten conjugate, hapten antibody, buffer (pH 6.0 to 8.5), a system for the determination of the $\beta$-galactosidase activity and possibly a definite amount of $\beta$-galactosidase antibody. The amount of the hapten conjugate is preferably 100 pM to 5 $\mu$M/liter, corresponding to 0.01 to 50 mU/test; the antibodies are preferably used as whole serum, concentrated or diluted down to $10^{-3}$.

In the case of this preferred reagent, the system for the determination of the enzyme activity preferably consists of a galactoside which carries an optically-determinable substituent which is split off by the $\beta$-galactosidase and can easily be determined optically. An example for such an optically-determinable substrate is o-nitrophenyl-$\beta$-D-galactoside (ONPG), which is preferably used in a concentration of 1 to 10 mM at 25° to 42° C.

The reagent according to the present invention is especially suitable for use in automatic analysers, including those which operate according to the centrifugal analysis principle. Because of the extremely high sensitivity, the amount of reagent used is small and this also applies to the amount of work required.

The following Examples are given for the purpose of illustrating the present invention:

EXAMPLE 1

Determination of thyroxin ($T_4$).
Buffer:
10 mM potassium phosphate, pH 7.0
0.14M sodium chloride
0.5 mM magnesium chloride
1 mM 1,4-dithiothreitol (DTT)
Reaction mixture:
10μ liter $T_4$-derivatised β-galactosidase 1 μg./ml. (prepared by the reaction of iodoacetyl-$T_4$ with β-galactosidase in a mole ratio of 1:2)
10μ liter anti-$T_4$ sheep whole serum, diluted to $10^{-1}$ (immunogen: $T_4$-edestin conjugate)
20μ liter L-thyroxin, 1.25 to 25 ng./liter The above mixture is incubated for 30 minutes at 37° C. and then heated for 5 minutes to 62° C. Subsequently, 70μ liter ONPG solution (o-nitrophenyl-β-D-galactoside; 3.3 mg./ml.) are added thereto. The mixture is maintained for 45 minutes at 37° C. and then 1 ml. 0.1M aqueous sodium carbonate solution is added thereto in order to stop the enzyme reaction. Subsequently, the liberated nitrophenol is measured at 405 nm. The amount of nitrophenol is inversely proportional to the amount of free $T_4$, which competes with the derivatised β-galactosidase for the stabilising antibody. FIG. 1 of the accompanying drawing shows graphically the calibration curve obtained in the case of different amounts of $T_4$ used according to the present invention. In this, the amount of $T_4$ used is given on the abscissa and the extinction at 405 nm is given on the ordinate.

EXAMPLE 2

The procedure described in Example 1 is used but, instead of $T_4$-derivatised β-galactosidase, there is used digoxin-derivatised β-galactosidase. This conjugate is prepared by reacting digoxin hydroxysuccinimide ester with β-galactosidase in a mole ratio of 20:1. The amount of anti-β-galactosidase serum used is 50μ liters, diluted to 1:100. The amount of anti-digoxin (sheep) is 50μ liters of an ammonium sulphate suspension dilute 1:5. For the immunisation, use is made of a digoxin-edestin conjugate.

The heat denaturing takes place by heating for 5 minutes to 62° C. The measurement of the ONPG takes place after 10 minutes at 37° C.

Figure 2:
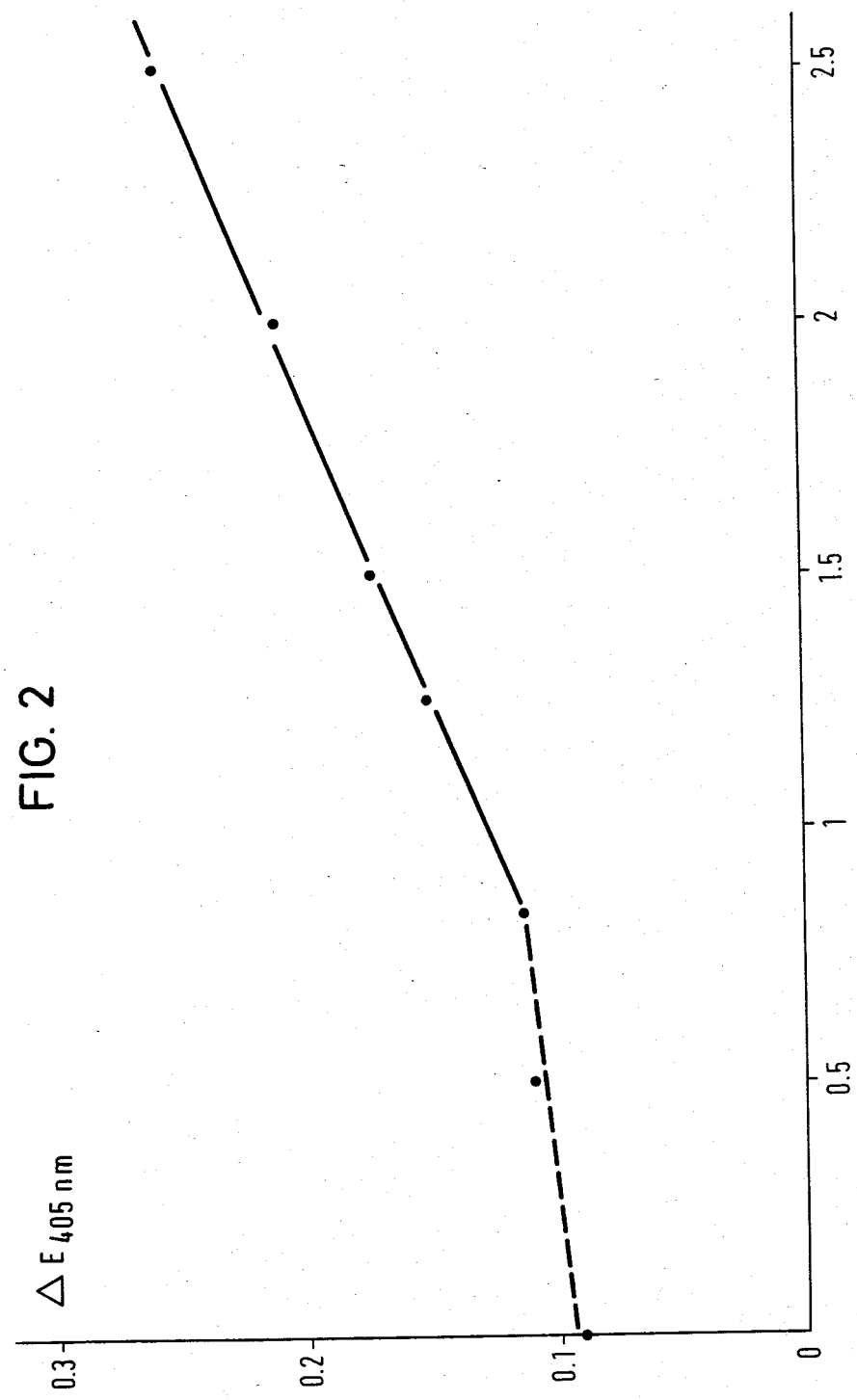

The calibration curve obtained with different amounts of digoxin standard solution is shown in FIG. 2 of the accompanying drawings. The amount of digoxin in pg. per 50μ liter of sample is given on the abscissa and the extinction difference at 405 nm on the ordinate.

It will be understood that the specification and examples are illustrative but not limitative of the present invention and that other embodiments within the spirit and scope of the invention will suggest themselves to those skilled in the art.

What is claimed is:

1. In a method for the determination of an antigen or hapten in a homogeneous aqueous phase by incubation of a test sample in the presence of antigen- or hapten-specific antibodies and of a defined amount of enzyme-marked antigen or hapten in a reaction solution and measurement of the activity of the marker enzyme, the improvement consisting of heating the reaction solution, after incubation, at temperature conditions and for a time sufficient to inactivate the marker enzyme by at least 50% in the absence of the antigen- or hapten-specific antibody and measuring the enzyme activity thereafter.

2. The method as claimed in claim 1, wherein enzyme-specific antibodies are additionally added for the incubation and the temperature and time conditions of the heating step are such that the marker enzyme is inactivated by at least 50% in the absence of the enzyme-specific antibody.

3. The method as claimed in claim 1, wherein the marker enzyme is one consisting of at least two subunits.

4. The method as claimed in claim 3, wherein the marker enzyme is β-galactosidase.

5. The method as claimed in claim 1, wherein an antigen is determined.

6. The method as claimed in claim 1, wherein a hapten is determined.

* * * * *